(12) United States Patent
Cummins (10) Patent No.: US 12,115,073 B2
(45) Date of Patent: Oct. 15, 2024

(54) ANTERIOR LUMBAR CAGE AND INSERTER DEVICE

(71) Applicant: Zavation Medical Products, LLC, Flowood, MS (US)

(72) Inventor: John Franklin Cummins, Kosciusko, MS (US)

(73) Assignee: ZAVATION MEDICAL PRODUCTS, LLC, Flowood, MS (US)

( * ) Notice: Subject to any disclaimer, the term of this patent is extended or adjusted under 35 U.S.C. 154(b) by 0 days.

(21) Appl. No.: 18/096,242

(22) Filed: Jan. 12, 2023

(65) Prior Publication Data

US 2024/0033090 A1 Feb. 1, 2024

Related U.S. Application Data

(63) Continuation of application No. 17/878,627, filed on Aug. 1, 2022, now Pat. No. 11,576,785.

(51) Int. Cl.
*A61F 2/44* (2006.01)
*A61F 2/30* (2006.01)
*A61F 2/46* (2006.01)

(52) U.S. Cl.
CPC ...... *A61F 2/30749* (2013.01); *A61F 2/30734* (2013.01); *A61F 2/447* (2013.01); *A61F 2/4611* (2013.01); *A61F 2002/30131* (2013.01); *A61F 2002/30331* (2013.01); *A61F 2002/30774* (2013.01); *A61F 2002/30795* (2013.01); *A61F 2002/30904* (2013.01); *A61F 2002/4629* (2013.01)

(58) Field of Classification Search
CPC .... A61F 2/447; A61F 2/4611; A61F 2/30749; A61F 2/30734; A61F 2002/30749; A61F 2002/30734; A61F 2002/30131; A61F 2002/30331; A61F 2002/30774; A61F 2002/30795; A61F 2002/30904; A61F 2002/4629
USPC ........ 623/17.11–17.16; 606/70–71, 280–299
See application file for complete search history.

(56) References Cited

U.S. PATENT DOCUMENTS

| | | |
|---|---|---|
| 9,408,715 B2 | 8/2016 | Donner et al. |
| 9,700,434 B2 | 7/2017 | Bae et al. |
| 9,872,780 B2 | 1/2018 | Reed |
| 9,974,664 B2 | 5/2018 | Emerick et al. |
| 10,004,608 B2 | 6/2018 | Carnes et al. |
| 10,105,236 B2 | 10/2018 | Donner et al. |

(Continued)

OTHER PUBLICATIONS

Notice of Allowance issued by the U.S. Patent and Trademark Office for the U.S. Appl. No. 17/878,627 on Oct. 27, 2022.

(Continued)

*Primary Examiner* — Jessica Weiss
(74) *Attorney, Agent, or Firm* — IP & T GROUP LLP (57) ABSTRACT

A plate and cage assembly for stabilization of vertebral bodies. The assembly includes at least one fixation member, a cage having a proximal wall, a superior surface and an inferior surface (the superior surface and the inferior surface for engaging adjacent vertebrae), and a plate coupled to the cage and having at least one hole traversing the plate at an angle for insertion of the at least one fixation member into one of the vertebral bodies. The proximal wall of the cage has a blind hole, and the plate has a threaded screw hole aligned with the blind hole in the proximal wall of the cage.

21 Claims, 8 Drawing Sheets

(56) References Cited

U.S. PATENT DOCUMENTS

| | | |
|---|---|---|
| 10,159,584 B2 | 12/2018 | Carnes et al. |
| 10,335,289 B2 | 7/2019 | Gamache et al. |
| 10,350,083 B2 | 7/2019 | Chataigner et al. |
| 10,369,015 B2 | 8/2019 | Gamache et al. |
| 10,524,929 B2 | 1/2020 | Shoshtaev |
| 10,561,504 B2 | 2/2020 | Padovani et al. |
| 10,667,925 B2 | 6/2020 | Emerick et al. |
| 10,687,964 B2 | 6/2020 | Bae et al. |
| 10,716,680 B2 | 7/2020 | Schmura et al. |
| 10,758,370 B2 | 9/2020 | Gilbride et al. |
| 10,786,369 B2 | 9/2020 | Carnes et al. |
| 10,806,592 B2 | 10/2020 | Donner et al. |
| 10,849,758 B2 | 12/2020 | Rathbun et al. |
| 10,898,345 B2 | 1/2021 | Bergey |
| 10,925,750 B2 | 2/2021 | Zappacosta et al. |
| 10,932,823 B2 | 3/2021 | Lauf et al. |
| 11,154,406 B2 | 10/2021 | Joly et al. |
| 11,246,715 B2 | 2/2022 | Dinville et al. |
| 11,273,058 B2 | 3/2022 | Ouidja et al. |
| 2009/0105832 A1 | 4/2009 | Allain |
| 2010/0185289 A1* | 7/2010 | Kirwan .................. A61F 2/447 |
| | | 623/17.11 |
| 2010/0305704 A1 | 12/2010 | Messerli et al. |
| 2010/0312346 A1* | 12/2010 | Kueenzi .................. A61F 2/44 |
| | | 623/17.16 |
| 2012/0197399 A1* | 8/2012 | Kirschman ............. A61F 2/447 |
| | | 623/17.11 |
| 2016/0151171 A1 | 6/2016 | Mozeleski et al. |
| 2016/0374831 A1 | 12/2016 | Duffield et al. |
| 2018/0303623 A1 | 10/2018 | Shoshtaev |
| 2019/0105175 A1* | 4/2019 | Zappacosta ........... A61F 2/4455 |
| 2020/0008958 A1 | 1/2020 | Gamache et al. |
| 2020/0121473 A1 | 4/2020 | Gamache et al. |
| 2020/0138595 A1 | 5/2020 | Shoshtaev et al. |
| 2020/0237529 A1 | 7/2020 | Padovani et al. |
| 2020/0246163 A1 | 8/2020 | Bae et al. |
| 2020/0281736 A1 | 9/2020 | Milz et al. |
| 2020/0289287 A1 | 9/2020 | Emerick et al. |
| 2020/0297511 A1 | 9/2020 | Gray et al. |
| 2020/0337854 A1 | 10/2020 | Schmura et al. |
| 2020/0352739 A1* | 11/2020 | Ouidja ................ A61F 2/30749 |
| 2021/0068982 A1 | 3/2021 | Carnes et al. |
| 2021/0077156 A1 | 3/2021 | Lauf et al. |
| 2021/0085488 A1 | 3/2021 | Murillo et al. |
| 2021/0154808 A1 | 5/2021 | Dash et al. |
| 2021/0322185 A1 | 10/2021 | Reed et al. |

OTHER PUBLICATIONS

Office Actioned issued by the U.S. Patent and Trademark Office for the U.S. Appl. No. 17/878,627 on Sep. 15, 2022.

* cited by examiner

ANTERIOR LUMBAR CAGE AND INSERTER DEVICE

CROSS-REFERENCE TO RELATED APPLICATIONS

This application is a continuation of U.S. Ser. No. 17/878,627 entitled "ANTERIOR LUMBAR CAGE AND INSERTER DEVICE," filed Aug. 1, 2022 (the entire contents of which are incorporated herein by reference).

BACKGROUND OF THE INVENTION

Field of the Invention

The present invention relates to implant devices for treating in particular spinal disorders.

Description of the Related Art

Disorders of the bone include disorders such as for example degenerative disc disease, disc herniation, osteoporosis, spondylolisthesis, stenosis, scoliosis (and other curvature abnormalities), kyphosis, tumor, fracture, arthritis, calcification, etc. Such disorders may result from factors including trauma, disease and degenerative conditions caused by injury and aging. Bone disorders typically result in symptoms including pain, nerve damage, and partial or complete loss of mobility. Additionally, severe pain and discomfort can occur due to the pressure exerted by bones on nerves.

A spinal disc can become damaged as a result of degeneration, dysfunction, disease and/or trauma. Conservative treatment can include non-operative treatment through exercise and/or pain relievers to deal with the pain. Operative treatment options include disc removal and replacement using an interbody spacers such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

The spacers are placed in the interdiscal space between adjacent vertebrae of the spine, resulting in spinal fusion of the adjacent vertebra wherein two or more vertebrae are joined together (fused) by way of interbody spacers, sometimes with bone grafting, to form a single bone. The current standard of care for interbody fusion requires surgical removal of all or a portion of the intervertebral disc. After removal of the intervertebral disc, the interbody spacer is inserted in the space between the adjacent vertebrae.

Ideally, the interbody spacer should stabilize the intervertebral space and allow fusion of the adjacent vertebrae. Moreover, during the time it takes for fusion to occur, the interbody spacer body should have sufficient structural integrity to withstand the stress of maintaining the space without substantially degrading or deforming and have sufficient stability to remain securely in place prior to actual bone ingrowth fusion.

The following provides a non-exhaustive list of implant devices and systems known in the art.

U.S. patent Ser. No. 10/758,370 (the entire contents of which are incorporated herein by reference) describes implant assemblies, systems, and methods for stabilizing a joint between a superior vertebra and an inferior vertebra. These systems included a plate member coupled to an interbody spacer with at least one fastener that extends superiorly or inferiorly from the implant assembly to anchor within a vertebral body and stabilize the joint. In the '370 patent, inserters were used to facilitate fixation of the various implant assemblies within the intervertebral space of the joint between the superior vertebra and the inferior vertebra.

U.S. Pat. Appl. Publ. No. 20210322185 (the entire contents of which are incorporated herein by reference) describes interbody fusion devices including deployable fixation members. The implant in the '185 publication included a spacer, optionally, an end member coupled to the spacer, and one or more fixation members configured to extend into adjacent vertebrae. The fixation members included screws, nails, shims, tangs, spikes, staples, pins, blades, fins, or the like, and combinations thereof.

U.S. patent Ser. No. 10/806,592 (the entire contents of which are incorporated herein by reference) describes arcuate fixation members with varying configurations provided, along with additional components for use in intervertebral implants. The arcuate fixation members in the '592 patent could be of different lengths, cross sectional geometries, and/or cross sectional areas.

U.S. patent Ser. No. 11/154,406 (the entire contents of which are incorporated herein by reference) describes an intervertebral implant comprising a body including a skeleton structure defining an interior cavity and including a plurality of openings into the interior cavity through walls defined by the skeleton structure; a lattice structure at least partially filling the interior cavity and extending into at least a portion of the plurality of openings; and a bone anchor including a curved plate body insertable into laterally elongated passage to anchor the intervertebral implant to an endplate of a vertebra.

U.S. Pat. Appl. Publ. No. 20200297511 (the entire contents of which are incorporated herein by reference) describes implantable systems, devices and related methods pertaining to spinal surgery. In the '511 publication, a low profile frame and spacer system was used for inserting into a disc space. The frame could receive different fixation devices, including threaded and non-threaded fixation devices.

U.S. patent Ser. No. 10/898,345 (the entire contents of which are incorporated herein by reference) describes an intervertebral implant including a body and a plate. The body has an upper surface defining an upper plane and a lower surface defining a lower plane. In the '345 patent, first and second fastener holes of the plate are configured to retain the heads of first and second fasteners. A portion of each of the shanks of the first and second fasteners extends from the first and second fastener holes beyond the upper plane. The shank portions of the first and second fasteners are curved in a direction away from the upper surface. A third fastener hole was configured to retain the head of the third fastener between the upper and lower planes. A portion of the shank of the third fastener extends from the third fastener hole beyond the lower plane. The shank portion of the third fastener is curved in a direction away from the lower surface.

U.S. Pat. Appl. Publ. No. 20210085488 (the entire contents of which are incorporated herein by reference) describes a fixation member inserter instrument which attached to an interbody spacer and assisted in the insertion of the interbody spacer into an intravertebral spacer. The distal end of the fixation member inserter instrument in the '488 publication included a fixation member guide with two or more fixation members that were configured to simultaneously deliver the two or more fixation members during the fixation member impaction process. The interbody spacer was attached to the inserter instrument by a threaded rod adjacent to the main body of the fixation member inserter instrument.

U.S. patent Ser. No. 11/246,715 (the entire contents of which are incorporated herein by reference) describes anchoring devices, anchoring systems for intervertebral implants, intervertebral implants, and instruments and methods for implanting implants. In the '715 patent, an anchoring device having a body comprising at least one curved plate elongated along a longitudinal axis was designed to be inserted through a passage crossing at least a part of implant, in order to penetrate into at least one vertebral endplate and attach implant onto this vertebral endplate.

U.S. patent Ser. No. 10/925,750 (the entire contents of which are incorporated herein by reference) describes stand-alone interbody fusion devices for engagement between adjacent vertebrae. The stand-alone interbody fusion devices of the '750 patent included a spacer or endplates and one or more inserts, members, or frames coupled to the spacer or endplates. The inserts, members, or frames were designed with apertures for bone fasteners, such as screws or anchors, to secure the implant to adjacent vertebrae.

U.S. patent Ser. No. 10/350,083 (the entire contents of which are incorporated herein by reference) describes intervertebral implants, anchoring devices for intervertebral implants, and implantation instrumentation. The anchoring device in the '083 patent had a body comprising at least one curve and a rigid plate elongated along a longitudinal axis so that its front end entered at least one vertebra while its rear end remained in the passage of an implant. In the '083 patent, the plate had at least one longitudinal slot separating at least one posterior portion of the plate into two branches.

U.S. patent Ser. No. 10/667,925 (the entire contents of which are incorporated herein by reference) describes interbody fusion devices, interbody fusion device systems, insertion tools, methods for assembling an interbody fusion device, and methods a method for inserting a medical device between two vertebral bodies. The interbody fusion device include a body member with a pivot cylinder, a superior member with a pivot channel that is configured to engage the pivot cylinder, and a movement mechanism for moving the superior member relative to the body member.

U.S. patent Ser. No. 10/524,929 (the entire contents of which are incorporated herein by reference) describes ALIF spine implants, ALIF installation instruments/tools, and ALIF procedures and ALIF installation instruments for an anterior lumbar interbody fusion (ALIF) surgical procedure. The ALIF implants had an ALIF cage and anchoring members. The ALIF installation instruments utilized a shaft having an inserter on one end that receives and holds an ALIF cage and anchoring members. The installation instrument allows insertion of the ALIF cage into a vertebral space, the anchoring members to be received in the ALIF cage, and then into vertebral bone.

SUMMARY OF THE INVENTION

In one embodiment, there is provided a plate and cage assembly for stabilization of vertebral bodies, comprising: at least one fixation member; a cage having a proximal wall, a superior surface and an inferior surface, the superior surface and the inferior surface for engaging adjacent vertebrae; and a plate coupled to the cage and having at least one hole traversing the plate at an angle for insertion of the at least one fixation member into one of the vertebral bodies. The proximal wall of the cage comprises a blind hole, and the plate has a threaded screw hole aligned with the blind hole in the proximal wall of the cage.

In another embodiment, there is provided an insertion device for insertion of a plate and cage assembly between vertebral bodies. The insertion device includes a carriage for holding at least one fastener member by at least one clip having two opposing resilient arms and two opposing clasps attached respectively to the two opposing resilient arms, wherein when a clip of the at least one clip slides over a body of a fastener member of the at least one fastener member, the resilient arms spread apart as the clasps engage the body of the fastener. Once the clasps are beyond the body of the fastener, resilient arms return inwardly toward each other to grasp the body of fastener.

In another embodiment, there is provided a method for stabilization of vertebral bodies. The method includes attaching an insertion device to a plate and cage assembly by way of a retention arm which penetrates past a plate and inserts in a blind hole in a proximal wall of a cage; inserting the plate and cage assembly into an intervertebral space between adjacent vertebra; holding fastener members in a carriage of the insertion device by way of clips holding the fastener members in place prior to insertion between adjacent vertebra; securing the fastener members into the adjacent vertebra; and detaching the insertion device from the plate and cage assembly.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawing, wherein.

DETAILED DESCRIPTION OF THE INVENTION

Embodiments of the disclosure are generally directed to intervertebral implant devices. One or more fixation members, such as screws, nails, shims, tangs, spikes, staples, pins, fins, blades, or the like, may be used to secure the implant devices to adjacent vertebrae. The fixation members may also include a combination of these to provide for optimal ease of insertion and fixation of the device. The intervertebral implant devices may be included with an inserter for placing the implant devices into the intervertebral space and securing the implant devices to the vertebrae with the fixation members.

The embodiments of the disclosure and the various features and advantageous details thereof are explained more fully with reference to the non-limiting embodiments and examples that are described and/or illustrated in the accompanying drawings and detailed in the following description. The features of one embodiment may be employed with other embodiments as the skilled artisan would recognize, even if not explicitly stated herein. Descriptions of well-known components and processing techniques may be omitted so as to not unnecessarily obscure the embodiments of the disclosure. The examples used herein are intended merely to facilitate an understanding of ways in which the disclosure may be practiced and to further enable those of skill in the art to practice the embodiments of the disclosure. Accordingly, the examples and embodiments herein should not be construed as limiting the scope of the disclosure. Moreover, it is noted that like reference numerals represent similar parts throughout the several views of the drawings.

Terms such as distal and proximal are used herein to designate the relative positions of components in relation to a particular view of the object designated, with proximal representing a part of the object closer and distal representing a part of the object farther removed from the proximal. These terms are used for clarity in description, but the examples and embodiments herein should not be construed to mean that the invention does not cover the same objects when viewed from a different perspective. Furthermore, in some cases (but not all), these terms may be synonymous with human body reference terms anterior and posterior.

In one embodiment of the present invention, there is provided a plate and cage assembly for stabilization of vertebral bodies, comprising: at least one fixation member; a cage having a proximal wall, a superior surface and an inferior surface, the superior surface and the inferior surface for engaging adjacent vertebrae; a plate coupled to the cage and having at least one hole traversing the plate at an angle for insertion of the at least one fixation member into one of the vertebral bodies, wherein the proximal wall of the cage comprises a blind hole, and the plate has a threaded screw hole aligned with the blind hole in the proximal r wall of the cage. The at least one fixation member can include nails, shims, pins, screws, etc.

Figure 1:
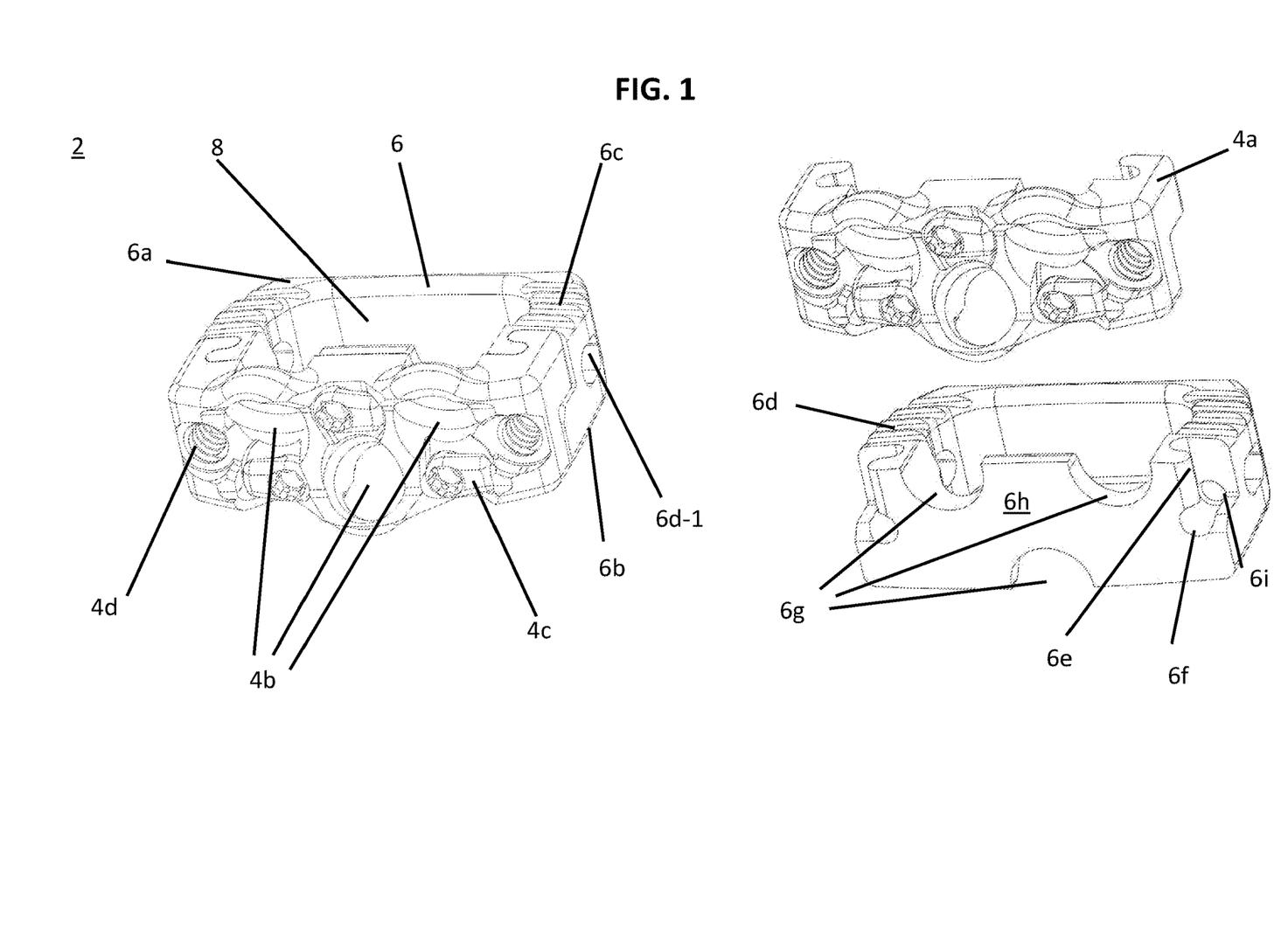
FIG. 1 is a representative depiction of one implant device of the present invention.

FIG. 1 is a representative depiction of one implant device of the present invention. In FIG. 1, a plate and cage assembly 2 is shown which are mechanically coupled to each other (as describe in more detail below). The plate and cage assembly 2 comprises a plate 4 and a cage 6. Cage 6 includes a vertically extending opening 8 for placement of bone graft material which extends all the way from superior surface 6a to inferior surface 6b. In one embodiment of the present invention, either one or both of the superior surface 6a and the inferior surface 6b have teeth (or corrugations) 6c for assisting in securing cage 6 once in between the vertebrae. In one embodiment of the present invention, sidewalls 6d include windows 6d-1. Windows 6d-1 assist with the filling of bone graft material in opening 8.

Figure 2:
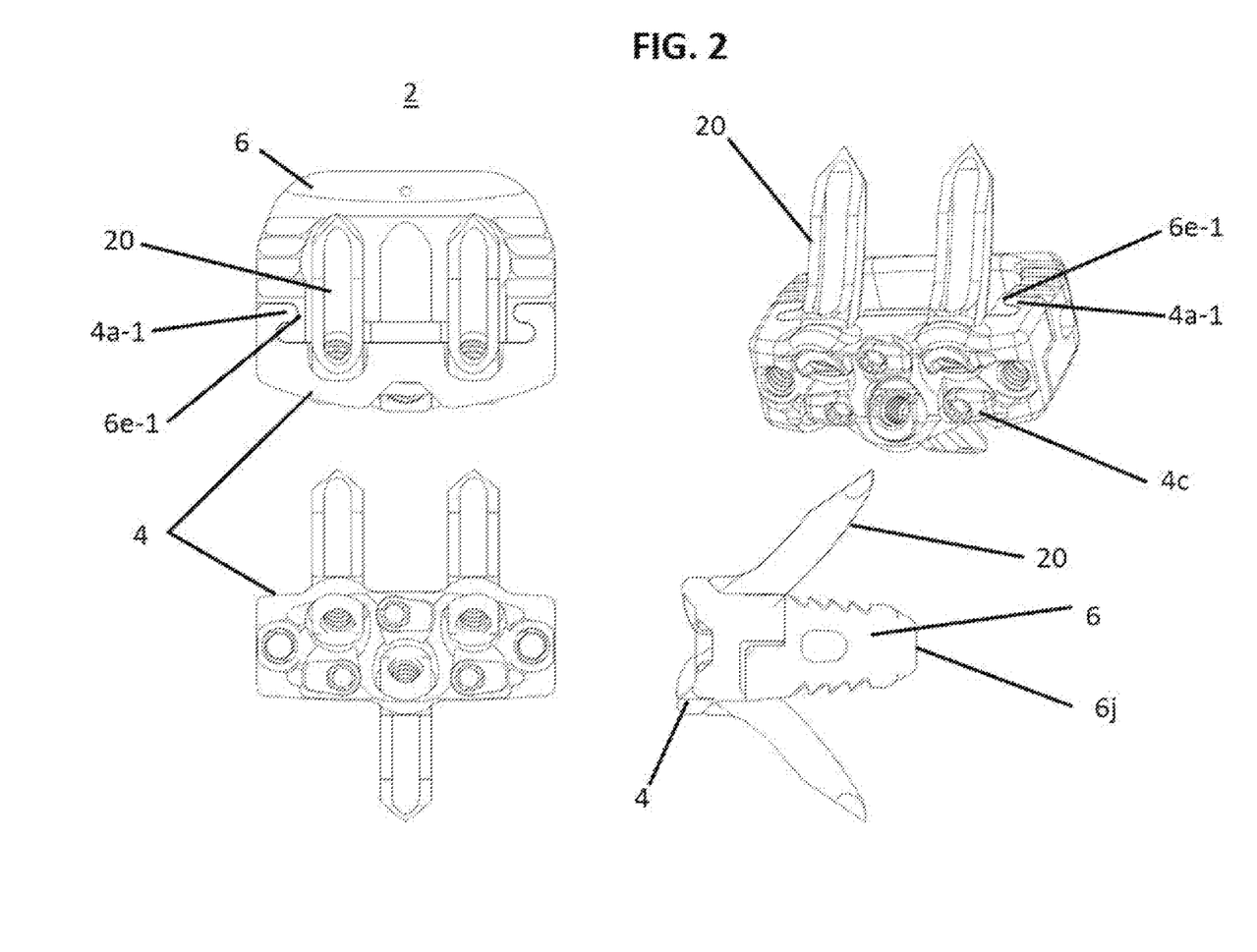
FIG. 2 is a depiction of the plate and cage assembly of the present invention showing fastening members extending therefrom.

In one embodiment of the present invention, cage 6 and plate 4 have complementary engagement structures 6e and 4a which couple the cage and plate together. Engagement structure 6e (in one example) is a vertically-rising engagement channel. This vertically-rising engagement channel in one embodiment does not extend all the way from the superior surface 6a to the inferior surface 6b, and instead a landing 6f is disposed at an intermediate position between the superior surface 6a to the inferior surface 6b. Engagement structure 4a (in one example) is a downwardly-extending flange 4a-1 which fits into the engagement channel 6e-1 of engagement structure 6e (as illustrated in FIG. 2).

In one embodiment of the present invention, cage 6 has openings 6g in a proximal wall 6h of cage 6. Accordingly, cage 6 has a distal wall 6j (shown in FIG. 2). Openings 6g provide clearance for a fastening member 20 (shown in FIG. 2) to pass through when being inserted into a vertebra. Similarly, plate 4 has openings 4b which provide clearance for a fastening member 20 (shown in FIG. 2) to pass through when being inserted into a vertebra. Openings 6g and openings 4b are preferably aligned, but regardless provide clearance for insertion of the fastening members 20.

In one embodiment of the present invention, plate 4 includes a retention tab 4c which is rotatable such that, once a fastening member is inserted into a vertebra, rotation of tab 4c prevents the fastening member from backing out from the vertebra. In one embodiment of the present invention, plate 4 includes at least two threaded screw holes 4d which can engage a threaded rod of an insertion tool (discussed below). In one embodiment of the present invention, the position of the screw holes 4d on plate 4 align with blind holes 6i above landings 6f. To be discussed in more detail later, a tip of the threaded rod of the insertion tool fits into one of the blind holes 6i such that, once in place, plate 4 and cage 6 cannot translate along the vertically-rising engagement channel of engagement structure 6e.

In one embodiment of the present invention, the implant devices disclosed herein are designed as an anterior lumbar interbody fusion ALIF implant product for implantation into an intervertebral space between vertebral bodies of a spine.

With minor changes to the size and shape of the plate and cage assembly, these implant device can be used in following spinal surgeries for anterior cervical interbody fusion, ACIF and lateral lumbar interbody fusion, LLIF (also know as DLIF and XLIF).

FIG. 2 is a depiction of the plate and cage assembly 2 showing fastening members 20 extending therefrom. As shown in FIG. 2, a fixation member in one embodiment of the present invention comprises a curved fixation member 20. In general, the fixation members of the present invention may be any type suitable for plate and cage attachment to the vertebrae, for example, nails, screws, pins, tacks, brads, spikes, cleats, or other suitable fixation members. However, in one aspect of the present invention, curved fixation members (once inserted) are less likely to back out of the vertebra and can better secure the plate and cage assembly 2 to the vertebrae than would a straight fixation member. In one embodiment of the present invention, a mixture of curved and straight fixation members may be used. In one embodiment of the present invention, three curved fixation members 20 are used with two in the upper half of plate 4 and one in the lower half of plate 4. The present invention is not limited to the number of fixation members, nor their relative distribution between the upper half of plate 4 and the lower half of plate 4.

Figure 3:
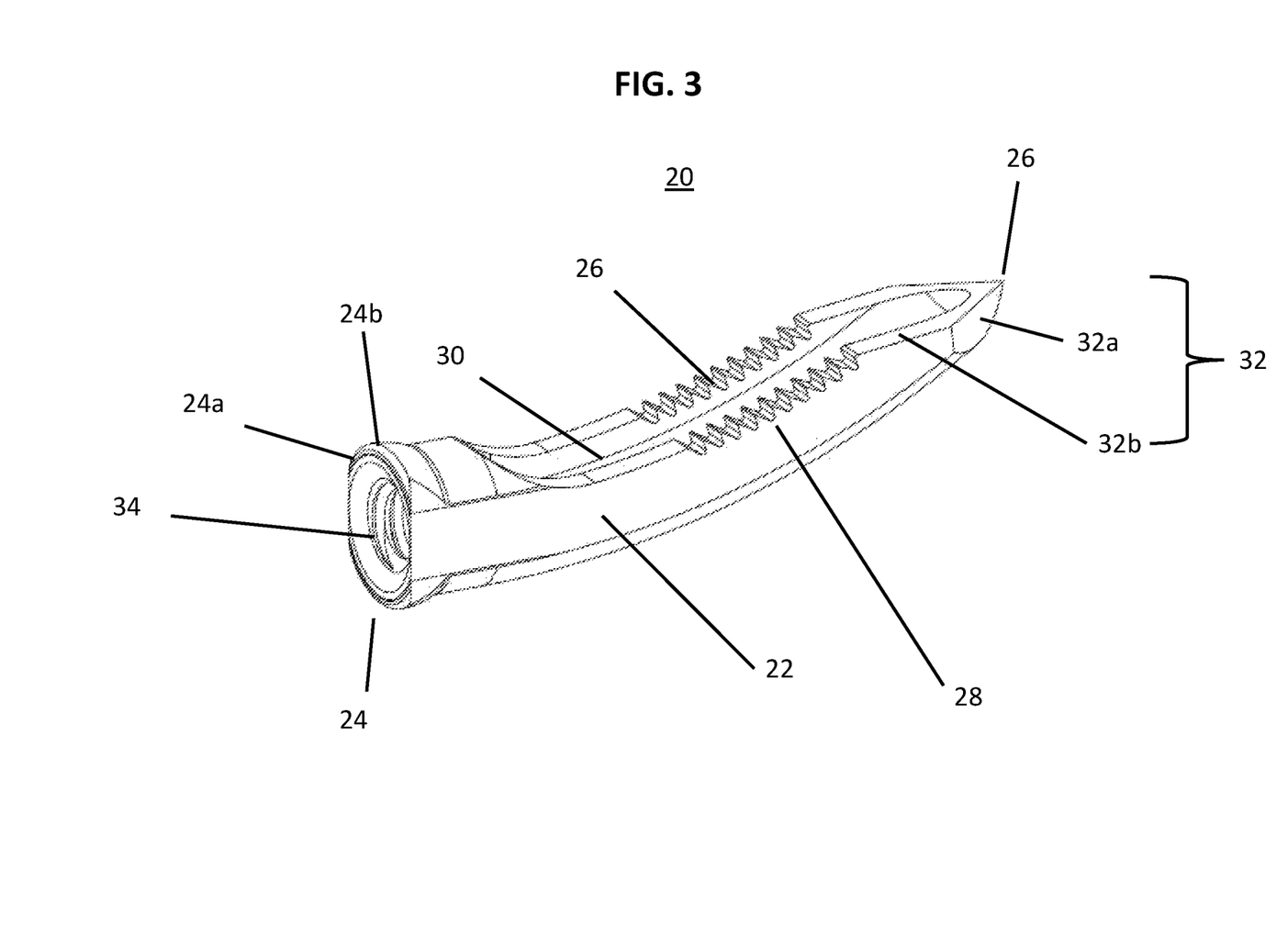
FIG. 3 is an enlarged depiction of a curved fastening member of the present invention.

FIG. 3 is an enlarged depiction of a curved fastening member 20. Curved fastening member 20 in one embodiment comprises a curved body 22 extending from a proximal end 24 to a distal end 26. Proximal end 24 may comprise an impact surface 24a for driving the curved fastening member 20 into the vertebra. Proximal end 24 may comprise a rim 24*b* which would engage with opening 4*b* in plate 4 and prevent the proximal end from traveling beyond plate 4. For example, the curved fastening member 20 (when hammered into a vertebral body) is stopped from penetrating too far into the vertebral body by the engagement of rim 24*b* with opening 4*b*. In one embodiment of the present invention, corrugations 26 are included on the curved fastening member 20. Corrugations 26 may also be used on non-curved fastening members. As illustrated in FIG. 3, corrugations 26 may be present on exterior sidewalls 28 separated from each other by channel 30. As illustrated in FIG. 3, distal end 26 may include a tapered bone piercing element 32 extending from an end of the corrugations to a tip of the distal end. The tapered bone piercing element 32 may (as shown in FIG. 3) have two tapered sections 32*a* and 32*b*, but the present invention is not so limited, and only one or more than two tapered sections can be used. Tapered section 32*a* extends from corrugations 26 and tapers down along a longitudinal direction. Tapered section 32*b* extends from tapered section 32*a* to the tip of the distal end, and tapers down along a longitudinal direction while tapering laterally to form a point. Furthermore, while the features in FIG. 3 are shown in the context of a curved fastening member, those features such as the proximal end 24, the distal end 26, impact surface 24*a*, the rim 24*b*, corrugations 26, exterior sidewalls 28, channel 30, and tapered bone piercing element 32 (including tapered sections 32*a* and 32*b*) are not limited to that of a curved fastening member but may likewise be used on a non-curved fixation member. As illustrated in FIG. 3 the curved fastening member may have a threaded hole 34 at the proximal end for removal of the fastening member from the vertebral body.

Figure 4:
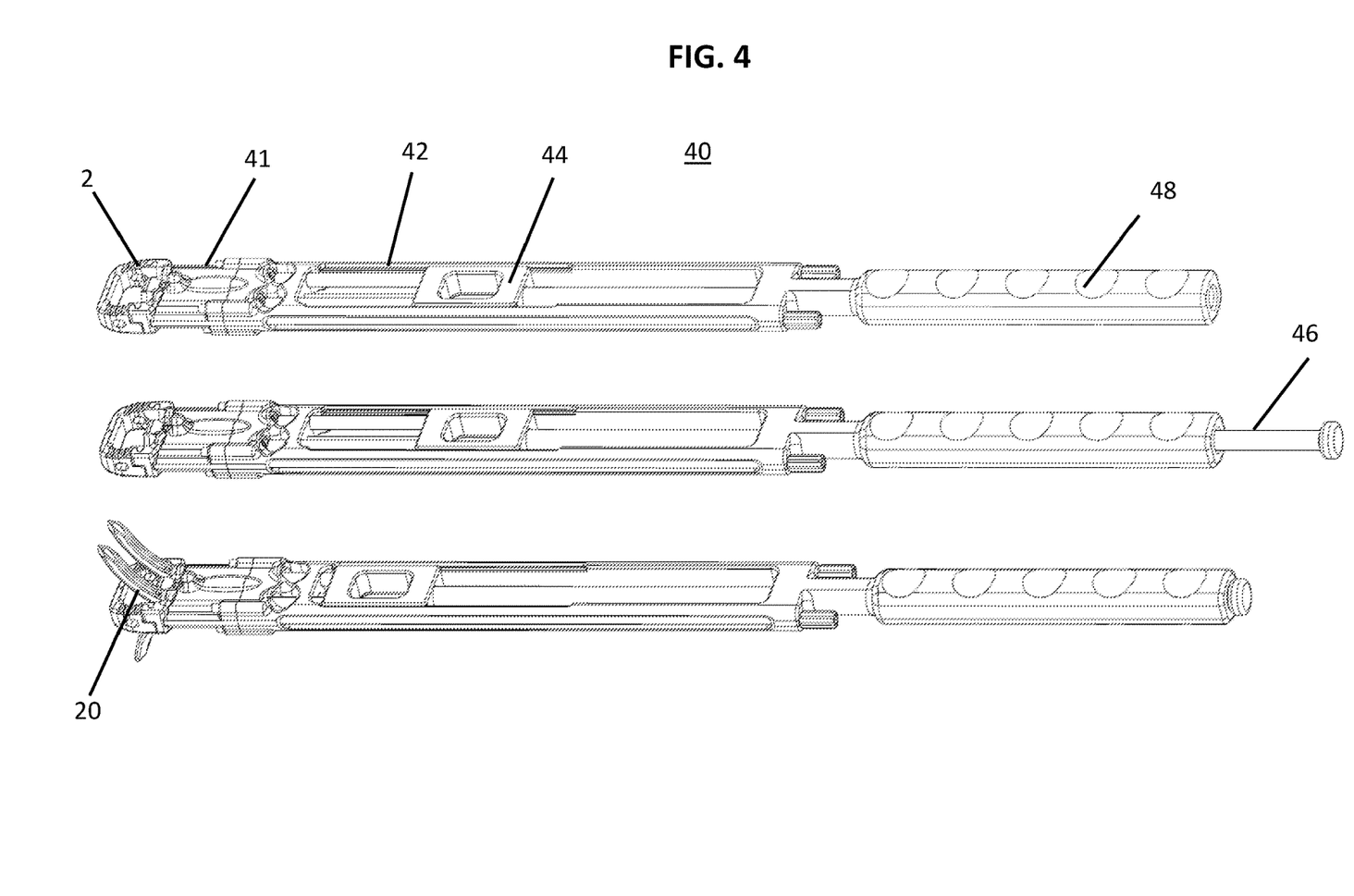
FIG. 4 is a depiction of an exemplary inserter device of the present invention showing the progression at the start of fastener deployment to the end of the nail fastener deployment.

FIG. 4 is a depiction of an exemplary inserter device of the present invention. In one embodiment of the present invention, an inserter device 40 is used to position the implant device (the plate and cage assembly 2) between adjacent vertebrae. Inserter device 40 shown in FIG. 4 holds fasteners (such as curved fastening members 20) in place in chamber housing 41 (prior to insertion into the adjacent vertebrae) and can drive the fasteners 20 along a curved path in chamber housing 41 and through openings 4*a* and 6*g* in the plate and cage assembly 2. In one embodiment of the present invention, inserter device 40 may have a carriage 41 having a superior channel and an inferior channel that are positioned such that the superior channel maintains two superior fasteners in alignment with openings 4*b* in the upper half of plate 4, and the inferior channel maintains an inferior fastener in alignment with opening 4*b* in the lower half of plate 4.

In one embodiment of the present invention, three curved fastener members 20 (such as shown in FIG. 2) are held in position by carriage 41 and then driven simultaneously into the vertebral disc space by way of three push rods 42 being pushed by bracket 44 which itself is translated by a push pin 46 (which can be pushed or hammered by medical personnel). In one embodiment of the present invention, the bracket comprises a slidable block for pushing the superior fasteners and the inferior fastener. In one embodiment of the present invention, insertion device 40 utilizes (for push rods 42) straight push rods for pushing curved fasteners 20 through carriage 41, through the plate and cage assembly 2, and into the superior and inferior vertebrae. In one embodiment of the present invention, bracket 44 is designed to drive all of the fixation members with a single impact to push pin 46. Insertion device 40 includes a handle 48 at the proximal end for holding and positioning insertion device 40.

FIG. 4 also shows the progression at the start of nail (or curved fastener) deployment to the end of the nail (or curved fastener) deployment. As the curved fastener is pushed (for example through and out of the carriage), straight push rod 42 contacts firstly a top edge of a proximal end of curved fastener 20 and thereafter, as curved fastener 20 is advanced, the straight push rod progressively contacts lower edges of the proximal end of curved fastener 20.

Figure 5:
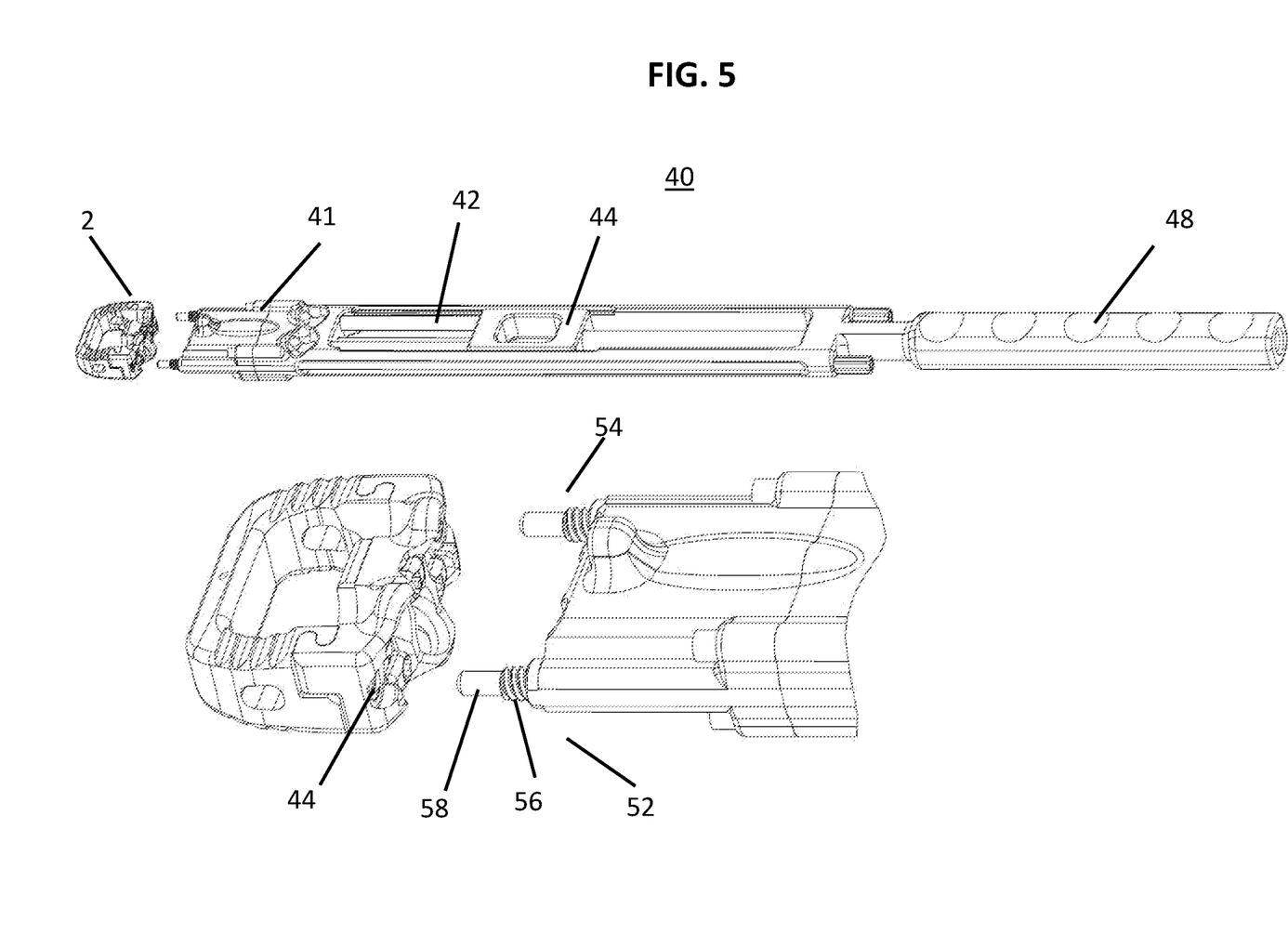
FIG. 5 is a depiction of the engagement of an inserter device of the present invention with the plate and cage assembly.

FIG. 5 is a depiction of the engagement of inserter device 40 of the present invention with the plate and cage assembly 2. In one embodiment of the present invention, inserter device 40 has a first implant retention arm 52 and a second implant retention arm 54. In one embodiment of the present invention, the first and second implant retention arms 52 and 54 engage opposing sides of the implant to removably couple the implant to the plate and cage assembly 2 to inserter device 40. While shown in FIG. 5 as having two retention arms, the present invention is not so limited and may include only a single retention arm or more than two retention arms.

As shown in FIG. 5, carriage 41 is coupled to the first and second implant retention arms 52 and 54. In one embodiment of the present invention, the first and second implant retention arms 52 and 54 each comprise threaded rod 56 with tip 58. Threaded rods 56 attach to screw holes 4*d* in plate 4. In one aspect of the present invention, the threaded rods 56 protruding from carriage 41 removably couple the inserter device 41 to the plate and cage assembly 2 by way of the screw holes 44 on opposite sides of a proximal end of plate 4.

Figure 6:
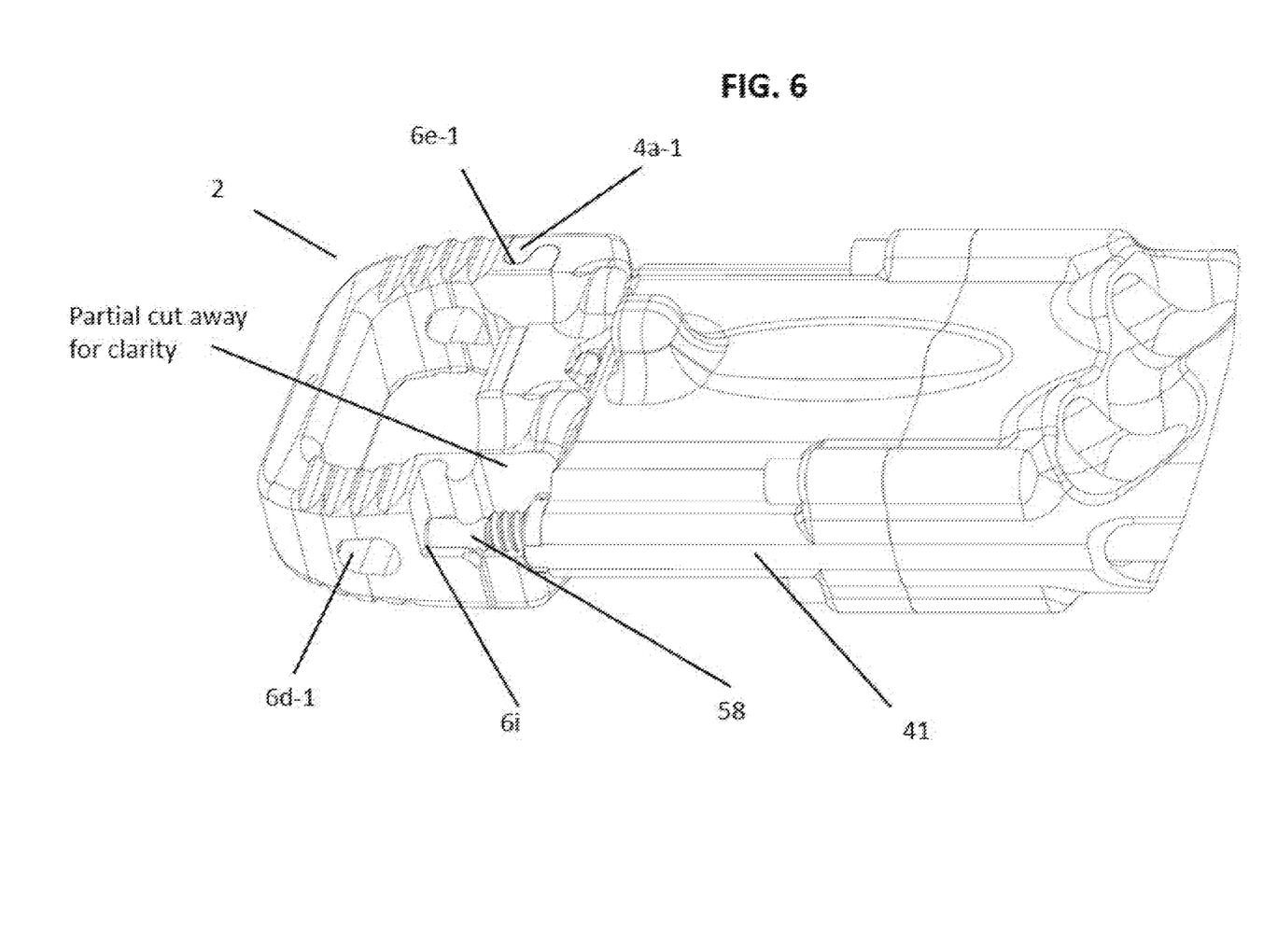
FIG. 6 is an enlarged depiction showing the coupling of the inserter device of FIG. 5.

As detailed above and as shown in FIG. 6, tip 58 of threaded rod 56 fits into one of the blind holes 6*i* in cage 6 such that, once in place, plate 4 and cage 6 cannot translate along the vertically-rising engagement channel of engagement structure 6*e*.

Figure 7:
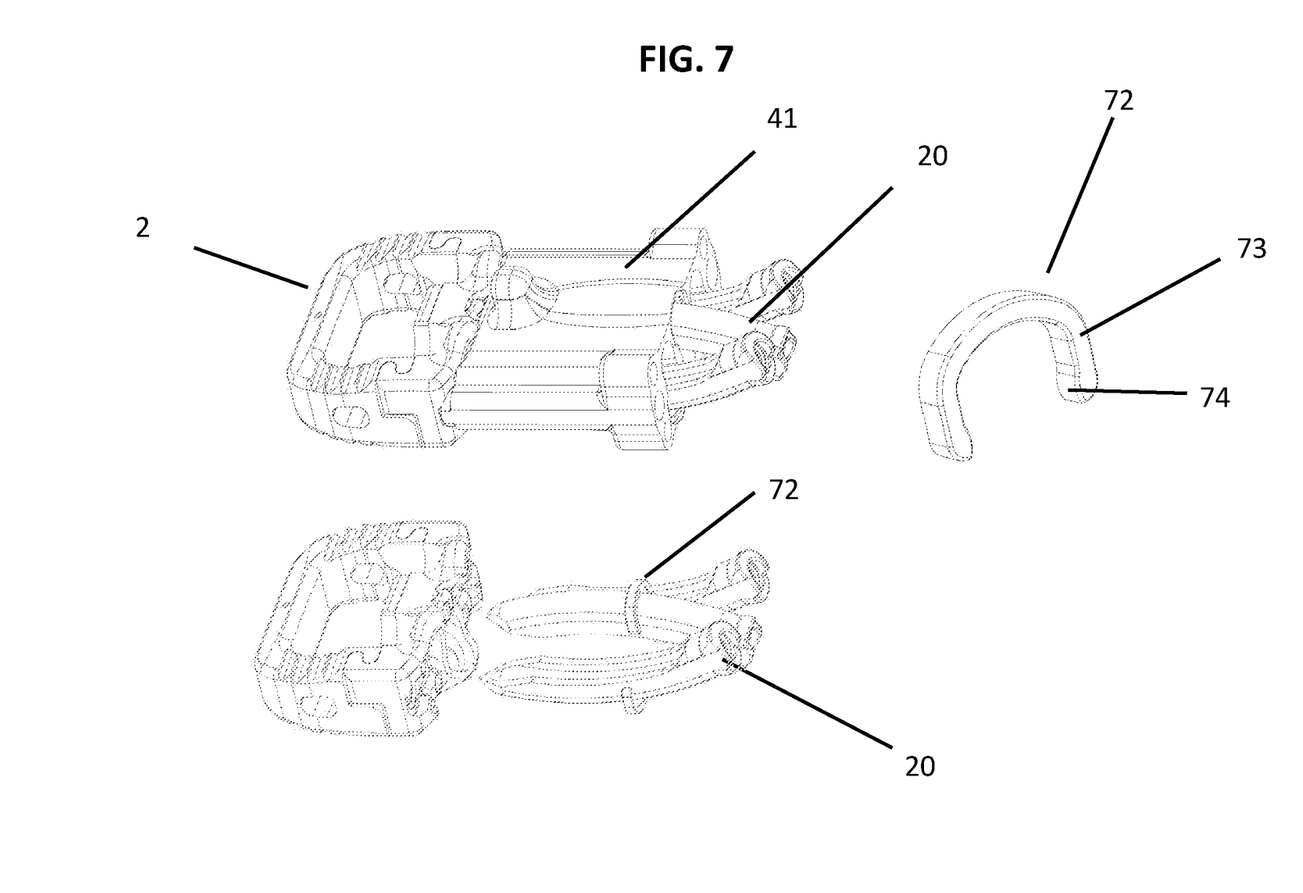
FIG. 7 is a depiction of the inserter device of the present invention where a carriage includes clips to hold the fasteners.

FIG. 7 is a depiction of one embodiment of the present invention where carriage 41 includes clips 72 to hold fasteners 20 in place prior to insertion of the fasteners 20 into the superior and inferior vertebrae. In this embodiment of the present invention, the fasteners 20 may be curved or non-curved fastener members. In one embodiment of the present invention, clips 72 have resilient clamp arms 73 and clasps 74 at an open end such that clips 72 can slide over fasteners 20 by way of spreading of clamp arms 73 as the clasps 74 engages the body of the fastener 20. Once clasps 74 are beyond the body of the fastener 20, clamp arms 73 return inwardly toward each other to grasp the body of fastener 20. As shown in FIG. 7, clips 72 abut a proximal end of carriage 41 and retain fastener members 20 at that position until the push rods 42 push the fastener members 20 through the plate and cage assembly 2 into the vertebrae.

In one embodiment of the invention, there is provided a system for stabilization of vertebrae. This system the implant(s) described above (for example the plate and cage assembly 2) and the insertion device described above. Typically, bone graft would be packed into to the window 6*d*-1 in the plate and cage assembly 2 prior to insertion between vertebrae. For example, bone graft may be inserted into the plate and cage assembly 2 through window 6*d*-1 after the plate and cage assembly 2 is attached to the insertion device 40.

Figure 8:
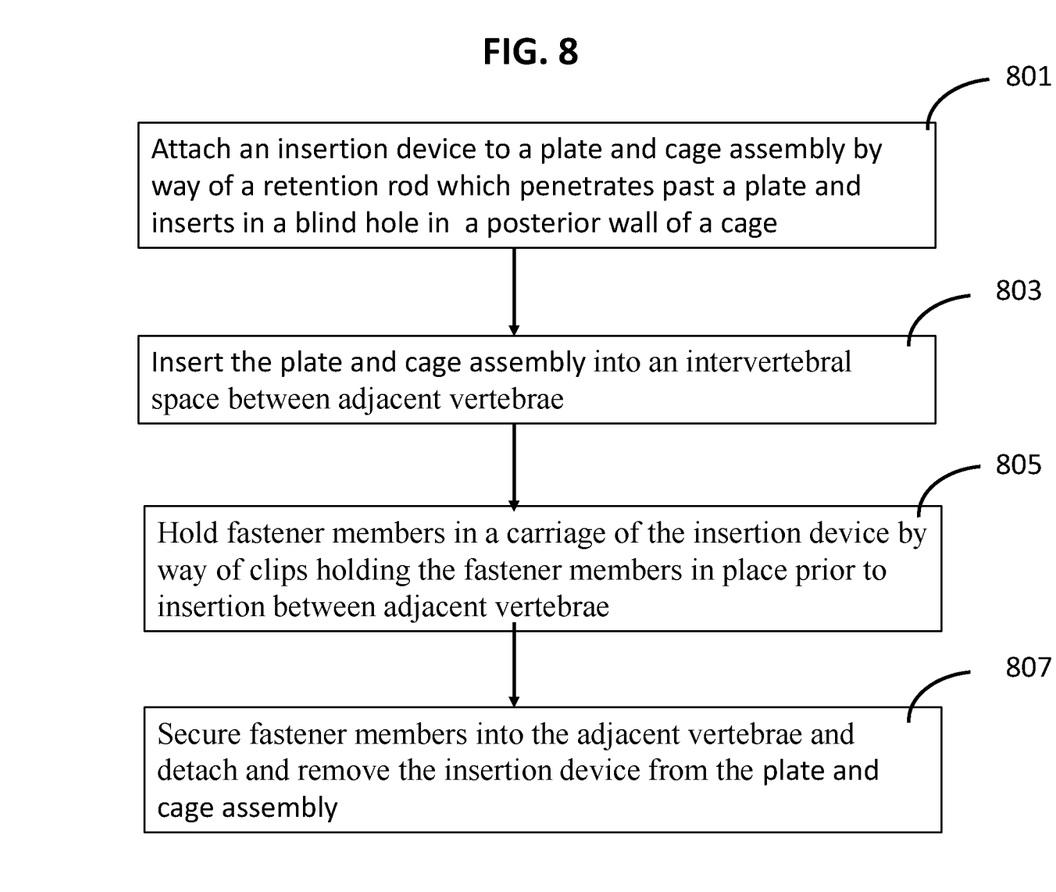
FIG. 8 is a flowchart depicting this method for stabilization of vertebrae.

In one embodiment, there is provided a method for stabilization of vertebrae. FIG. 8 is a flowchart depicting this method for stabilization of vertebrae. This method at 801 attaches an insertion device to any of the plate and cage assemblies described above, and in particular attaches an insertion device to a plate and cage assembly by way of a retention arm which penetrates past a plate in inserts in a blind hole in a proximal wall of a cage.

At 803, insert the plate and cage assembly into an intervertebral space between adjacent vertebrae.

At 805, hold (curved) fastener members in a carriage of the insertion device by way of clips holding the fastener members in place prior to insertion between adjacent vertebrae.

At 807, secure the (curved) fastener members into the adjacent vertebrae and detach and remove the insertion device from the plate and cage assembly.

This invention is not limited to a specific type of bone graft material. In general, a variety of bone graft materials are known and suitable for this invention. These typically comprise calcium phosphate-based or gel-based materials. Polymer-based bone graft substitutes containing (or not containing) collagen can be used. Ceramic bone graft substitutes can be used. In one embodiment, the implantable bone graft material comprises a composite of a ceramic and a polymer. The ceramic and the polymer can be present at a weight ratio ranging from about 10:1 ceramic to polymer to about 2:1 ceramic to polymer. Alternatively, the weight ratio of the ceramic to the polymer can range from about 2:1 (about 66% ceramic to about 33% polymer), from about 3:1 (about 75% ceramic to about 25% polymer), from about 4:1 (about 80% ceramic to about 20% polymer), from about 9:1 (about 90% ceramic to about 10% polymer), from about 10:1 (about 99% ceramic to about 1% polymer). Other bone graft materials besides those specifically listed above can be used.

This invention is also not limited to the type of material that the implant device is made of. The implant devices of the present invention can be made of any material appropriate for human implantation and having the mechanical properties sufficient to be utilized for the intended purpose of spinal fusion, including various metals such as cobalt chrome, stainless steel or titanium including its alloys, various plastics including those which are bio-absorbable, and various ceramics or combination sufficient for the intended purpose. Further, the implants of this invention may be made of a solid material, a mesh-like material, a porous material and may comprise, wholly or in part, materials capable of directly participating in the spinal fusion process, or be loaded with, composed of, treated of coated with chemical substances such as bone, morphogenic proteins, hydroxyapatite in any of its forms, and osteogenic proteins, to make them bioactive for the purpose of stimulating spinal fusion. The implants of this invention may be wholly or in part bioabsorbable. Other materials for the implant device besides those specifically listed above can be used.

This invention is also not limited to the methods by which the implant devices are made. The individual components can be machined from solid stock pieces. Molding can be used to make the individual components. In this case, machining to final dimensions may or may not be in order. The surfaces once properly dimensioned can be coated with a variety of biocompatible coatings and/or surface treatments. Various coatings include for example calcium phosphate ceramics, such as tricalcium phosphate (TCP) and hydroxyapatite (HA), and hydroxyapatite (a naturally occurring material in bone). Moreover, surfaces of the implant device that contact bone may be treated to promote fusion of the implant to the bone. Treatment may include, but is not limited to, applying a hydroxyapatite coating on contact surfaces, spraying a titanium plasma on contact surfaces, and/or texturing the contact surfaces by scoring, peening, implanting particles in the surfaces, or otherwise roughening the surfaces of the implant.

In some embodiments, any of the implants and insertion devices described above can be used with additional implants and instruments. In some embodiments, the implants and instruments can be used with stabilization members, such as plates, screws, and rods. In addition, a multi-level construct can be formed, wherein any one or more of the implant devices described above can be used on one level, while a similar or different implant (e.g., fusion or prosthetic) can be used on a different level.

Statements of the Invention

The following are non-limiting statements of the invention describing various aspects of the invention.

Statement 1. A plate and cage assembly for stabilization of vertebral bodies, comprising:
at least one fixation member;
a cage having a proximal wall, a superior surface and an inferior surface, the superior surface and the inferior surface for engaging adjacent vertebrae; and
a plate coupled to the cage and having at least one hole traversing the plate at an angle for insertion of the at least one fixation member into one of the vertebral bodies,
wherein
the proximal wall of the cage comprises a blind hole,
the plate has a threaded screw hole aligned with the blind hole in the proximal wall of the cage.

Statement 2. The assembly of statement 1, wherein the cage and the plate comprise respectively an engagement channel and an engagement flange for securing the cage and the plate together.

Statement 3. The assembly of any of the statements above, wherein, to further secure the engagement channel and the engagement flange from separation, a retention arm extends through the threaded screw hole in the plate and into the blind hole of the cage.

Statement 4. The assembly of any of the statements above, further comprising corrugations on at least one of the superior surface and the inferior surface of the cage.

Statement 5. The assembly of any of the statements above, wherein the least one fixation member comprises a curved fixation member.

Statement 6. The assembly of any of the statements above, wherein the curved fixation member comprises:
a proximal end and a distal end having a tapered bone piercing element.

Statement 7. The assembly of any of the statements above, wherein the curved fixation member comprises corrugations disposed on exterior sidewalls of the curved fixation member, the exterior sidewalls separated from each other by a channel extending along a length of the curved fixation member.

Statement 8. The assembly of any of the statements above, wherein
the tapered bone piercing element comprises a first tapered section and a second tapered section,
the first tapered section extending from the corrugations to the second tapered section;
the second tapered section extending from the first tapered section to a tip of the first tapered section.

Statement 9. The assembly of any of the statements above, wherein the curved fixation member comprises:

a rim at the proximal end for stopping against the at least one hole of the plate when the fixation member is driven into a vertebra.

Statement 10. The assembly of any of the statements above, wherein the curved fixation member comprises: a threaded hole in the proximal end for attached to the curved fixation member for removal from a vertebra.

Statement 11. An insertion device for insertion of a plate and cage assembly between vertebral bodies (including but not limited to any of the plate and cage assemblies set forth in statements 1-10), comprising:
  a carriage for holding at least one fixation member by at least one clip having two opposing resilient arms and two opposing clasps attached respectively to the two opposing resilient arms,
  wherein, when a clip of the at least one clip slides over a body of a fixation member of the at least one fixation member, the resilient arms spread apart as the clasps engage the body of the fixation member, and once the clasps are beyond the body of the fixation member, the resilient arms return inwardly toward each other to grasp the body of fixation member;
  a handle for holding the insertion device;
  push rods for pushing the at least one fixation member through the carriage, through the plate and cage assembly, and into the vertebral bodies;
  a bracket coupled to the push rods; and
  a push pin for driving the bracket.

Statement 12. The insertion device of statement 11, further comprising a retention arm for coupling the carriage to the plate and cage assembly.

Statement 13. The insertion device of statements 11 or 12, wherein the retention arm comprises a) a threaded section for threading into a threaded hole in the plate of the plate and cage assembly and b) a tip for insertion into a blind hole in a cage of the plate and cage assembly.

Statement 14. The insertion device of any of statements 11-13, wherein
  the cage attached to the insertion device has a proximal wall, a superior surface and an inferior surface, the superior surface and the inferior surface for engaging adjacent vertebrae;
  the plate attached to the insertion device is coupled to the cage and has at least one hole traversing the plate at an angle for insertion of the at least one fixation member into one of the vertebral bodies.

Statement 15. The insertion device of, wherein the push rods comprise three rods arranged to push a) two superior fasteners of any of statements 11-14 the at least one fixation member and b) an inferior fastener of the at least one fixation member into the vertebral bodies simultaneously.

Statement 16. The insertion device of any of statements 11-15, wherein the bracket comprises a slidable block for pushing the superior fasteners and the inferior fastener.

Statement 17. The insertion device of any of statements 11-16, wherein at least one of the superior fasteners and the inferior fastener comprises a curved fastener held by the clip.

Statement 18. The insertion device of any of statements 11-17, wherein at least one of the push rods comprises a straight push rod which pushes the curved fastener out of the carriage.

Statement 19. The insertion device of any of statements 11-18, wherein pushing the curved fastener out of the carriage occurs with the straight push rod contacting firstly a top edge of a proximal end of the curved fastener and thereafter, as the curved fastener is advanced, the straight push rod progressively contacts lower edges of the proximal end of the curved fastener.

Statement 20. The insertion device of any of statements 11-19, wherein the push pin is hammered to drive simultaneously multiple of the at least one fixation members into the vertebral bodies.

Statement 21. A method for stabilization of vertebrae, comprising:
  attaching an insertion device (including but not limited to any of the insertion devices set forth in statements 11-20) to a plate and cage assembly (including but not limited to any of the plate and cage assemblies set forth in statements 1-10) by way of a retention arm which penetrates past a plate and inserts in a blind hole in a proximal wall of a cage;
  inserting the plate and cage assembly into an intervertebral space between adjacent vertebrae;
  holding fastener members in a carriage of the insertion device by way of clips holding the fastener members in place prior to insertion between adjacent vertebrae;
  securing the fastener members into the adjacent vertebrae; and
  detaching the insertion device from the plate and cage assembly.

Numerous modifications and variations of the present invention are possible in light of the above teachings. It is therefore to be understood that within the scope of the appended claims, the invention may be practiced otherwise than as specifically described herein.

The invention claimed is:
1. A plate and cage assembly for stabilization of adjacent vertebral bodies, comprising:
  at least one bone fastener;
  a cage having a proximal wall, a distal wall, opposing sidewalls, a superior surface and an inferior surface, the superior surface and the inferior surface for respectively engaging the adjacent vertebral bodies; and
  a plate coupled to the cage at the proximal wall, the plate having at least one hole traversing the plate at an angle for insertion of the at least one bone fastener into one of the adjacent vertebral bodies,
  wherein:
  the proximal wall of the cage has disposed therein an engagement hole for engaging a tip portion of a retention arm for removably coupling to the cage,
  the proximal wall of the cage has at least one opening for engaging the at least one bone fastener,
  the plate has an alignment hole aligned with the engagement hole in the proximal wall of the cage,
  the engagement hole a) is disposed inside a first opposing side wall, of the opposing side walls, that connects to the distal wall and b) extends in a longitudinal direction at least partially through the first opposing side wall, and
  upon engagement of the tip portion of the retention arm into the engagement hole, the tip portion a) extends beyond the alignment hole in the plate and b) extends into the engagement hole inside the first opposing side wall that connects to the distal wall, and thereby prevents vertical displacement of the plate relative to the cage.

2. The plate and cage assembly of claim 1, wherein respective centers of the engagement hole in the proximal wall of the cage and the alignment hole in the plate lie on a common axis extending away from the proximal wall.

3. The plate and cage assembly of claim 2, wherein, when the tip portion of the retention arm engages the engagement hole, the engagement hole in the proximal wall of the cage, the alignment hole in the plate, and the tip portion of the retention arm lie on the common axis.

4. The plate and cage assembly of claim 1, wherein
the cage and the plate comprise respectively a) an engagement channel extending partially from the superior surface to the inferior surface and b) an engagement flange which slides into the engagement channel.

5. The plate and cage assembly of claim 4, wherein
the engagement channel of the cage is disposed on a proximal side of the cage adjacent the plate and is open to the superior surface such that the cage and the plate are secured together by sliding the engagement flange of the plate a) toward the inferior surface, b) into the engagement channel on the proximal side of the cage and c) against a landing at an intermediate position between the superior surface and the inferior surface.

6. The plate and cage assembly of claim 1, further comprising a retention member on the plate for preventing the at least one bone fastener from backing out from the one of the adjacent vertebral bodies.

7. The plate and cage assembly of claim 1, further comprising corrugations on at least one of the superior surface and the inferior surface of the cage.

8. The plate and cage assembly of claim 1, wherein the least one bone fastener comprises a curved bone fastener.

9. The plate and cage assembly of claim 8, wherein the curved bone fastener comprises:
a proximal end, and
a distal end having a tapered bone piercing element.

10. The plate and cage assembly of claim 8, wherein the curved bone fastener comprises corrugations disposed on exterior sidewalls of the curved bone fastener member, the exterior sidewalls separated from each other by a channel extending along a length of the curved bone fastener.

11. The plate and cage assembly of claim 10, wherein
the tapered bone piercing element comprises a first tapered section and a second tapered section,
the first tapered section extends from the corrugations to the second tapered section; and
the second tapered section extends from the first tapered section to a tip of the first tapered section.

12. The plate and cage assembly of claim 8, wherein the curved bone fastener comprises:
a rim at the proximal end for stopping against the at least one hole of the plate when the curved bone fastener is driven into one of the adjacent vertebral bodies.

13. The plate and cage assembly of claim 8, wherein the curved bone fastener comprises:
a threaded hole in the proximal end for removal of the curved bone fastener from a vertebra.

14. A system for insertion of a plate and cage assembly between adjacent vertebral bodies,
the system comprising a plate and cage assembly and an insertion device;
wherein the plate and cage assembly includes:
at least one bone fastener;
a cage having a proximal wall, a distal wall, opposing sidewalls, a superior surface and an inferior surface, the superior surface and the inferior surface for respectively engaging the adjacent vertebral bodies; and
a plate coupled to the cage at the proximal wall, the plate having at least one hole traversing the plate at an angle for insertion of the at least one bone fastener into one of the adjacent vertebral bodies,
wherein:
the proximal wall of the cage has disposed therein a blind engagement hole,
the proximal wall of the cage has at least one opening for engaging the at least one bone fastener, and
the plate has a threaded alignment hole aligned with the blind engagement hole in the proximal wall of the cage, and
wherein the insertion device includes:
a retention arm which is removably coupled to the plate and cage assembly, the retention arm comprising a tip portion for removably coupling to the cage, wherein engagement of the tip portion of the retention arm into the blind engagement hole in the proximal wall of the cage prevents vertical displacement of the plate relative to the cage;
a carriage for holding the at least one bone fastener by at least one clip having two opposing resilient arms and two opposing clasps attached respectively to the two opposing resilient arms;
a handle for holding the insertion device;
push rods for pushing the at least one bone fastener through the carriage, through the plate and cage assembly, and into at least one of the adjacent vertebral bodies;
a bracket coupled to the push rods; and
a push pin for driving the bracket.

15. The system of claim 14, wherein the push rods comprise three rods arranged to push a) two superior bone fasteners of the at least one bone fastener and b) an inferior bone fastener of the at least one bone fastener into the adjacent vertebral bodies simultaneously.

16. The system of claim 15, wherein the bracket comprises a slidable block for pushing the two superior bone fasteners and the inferior bone fastener.

17. The system of claim 15, wherein at least one of the two superior bone fasteners and the inferior bone fastener comprises a curved fastener held by the at least one clip.

18. The system of claim 17, wherein at least one of the three rods comprises a straight push rod which pushes the curved fastener out of the carriage.

19. The system of claim 18, wherein, when pushing the curved fastener out of the carriage occurs, the straight push rod contacts firstly a top edge of a proximal end of the curved fastener and thereafter, as the curved fastener is advanced, the straight push rod progressively contacts lower edges of the proximal end of the curved fastener.

20. A method for stabilization of adjacent vertebral bodies using the plate and cage assembly of claim 1, comprising:
attaching an insertion device to the plate and cage assembly;
inserting the plate and cage assembly into an intervertebral space between two adjacent vertebral bodies;
holding fastener members including the at least one bone fastener in the carriage of the insertion device by way of the at least one clip comprising multiple clips holding the fastener members in place prior to insertion in between the two adjacent vertebral bodies;
securing each of the fastener members into a respective one of the two adjacent vertebral bodies; and
detaching the insertion device from the plate and cage assembly.

21. An insertion device for insertion of the plate and cage assembly of claim 1 between adjacent vertebral bodies, comprising:
- at least one retention arm removably coupled to the plate and cage assembly;
- at least one bone fastener;
- at least one clip having two opposing resilient arms and two opposing clasps attached respectively to the two opposing resilient arms;
- a carriage for holding the at least one bone fastener by the at least one clip having the two opposing resilient arms and the two opposing clasps;
- a handle for holding the insertion device;
- push rods for pushing the at least one bone fastener through the carriage, through the plate and cage assembly, and into at least one of the adjacent vertebral bodies;
- a bracket coupled to the push rods; and
- a push pin for driving the bracket.

* * * * *